US006426069B1

(12) United States Patent
Yesair

(10) Patent No.: US 6,426,069 B1
(45) Date of Patent: Jul. 30, 2002

(54) METHOD AND COMPOSITIONS FOR INCREASING INTESTINAL ABSORPTION OF FATS

(75) Inventor: David W. Yesair, Byfield, MA (US)

(73) Assignee: BioMolecular Products, Inc., Byfield, MA (US)

( * ) Notice: Subject to any disclaimer, the term of this patent is extended or adjusted under 35 U.S.C. 154(b) by 0 days.

(21) Appl. No.: 09/786,695
(22) PCT Filed: Sep. 7, 1999
(86) PCT No.: PCT/US99/20427
§ 371 (c)(1),
(2), (4) Date: Jun. 11, 2001
(87) PCT Pub. No.: WO00/13689
PCT Pub. Date: Mar. 16, 2000

Related U.S. Application Data

(60) Provisional application No. 60/099,430, filed on Sep. 8, 1998.
(51) Int. Cl.⁷ .................. A61K 38/46; A61K 38/00
(52) U.S. Cl. .................. 424/94.6; 514/12; 514/77; 514/182; 514/738
(58) Field of Search .................. 514/12, 77, 182, 514/738; 424/94.6

(56) References Cited

U.S. PATENT DOCUMENTS

| 4,849,132 A | 7/1989 | Fujita et al. |
| 4,874,795 A | 10/1989 | Yesair |
| 5,314,921 A | 5/1994 | Yesair |
| 5,571,517 A | 11/1996 | Yesair |
| 5,707,873 A | 1/1998 | Yesair |
| 5,716,814 A | 2/1998 | Yesair |
| 5,741,822 A | 4/1998 | Yesair |

FOREIGN PATENT DOCUMENTS

WO    WO 98/10776 A1    3/1998

OTHER PUBLICATIONS

Gaskin et al., *Pediatric Pulmonology* 139–140 (2001).
Sternby and Nilsson, *Scand J Gastroenterol* 32:261–267 (1997).
Ramsammy and Brockerhoff, *J. Biol. Chem.* 257: 3570–3574 (1982).

*Primary Examiner*—Rebecca Cook
(74) *Attorney, Agent, or Firm*—Wolf, Greenfield & Sacks, P.C.

(57) ABSTRACT

This invention provides a composition and method for increasing fat absorption from the intestine by increasing the amount of lysophosphatidylcholine in the intestine. The composition comprises phospholipase $A_2$ and lipid molecules.

5 Claims, No Drawings

METHOD AND COMPOSITIONS FOR INCREASING INTESTINAL ABSORPTION OF FATS

RELATED APPLICATIONS

This application claims the benefit under 35 U.S.C. §120 or 35 U.S.C. §365(c) of PCT International application PCT/US99/20427, designating the United States, and filed Sep. 7, 1999. PCT application PCT/US99/20427, of which this application is a national stage filing under 35 U.S.C. §371, was published under PCT Article 21(2) in English.

Application number PCT/US99/20427 claims the benefit under 35 U.S.C. §119(e) of U.S. provisional application No. 60/099,430, filed Sep. 8, 1998.

FIELD OF THE INVENTION

This invention relates generally to the field of lipid metabolism, and more specifically to the field of absorption of lipids from the gut.

BACKGROUND OF THE INVENTION

The absorption of lipid molecules from the intestinal tract is hindered in certain disease conditions, including cystic fibrosis (CF), Graves disease, celiac disease, diabetes mellitus, and cachexia. This malabsorption of dietary fats can manifest itself in excess fat in the stools, a condition known as steatorrhea. Fat absorption in cystic fibrosis patients can be severely affected and 30 to 60 percent of ingested fat can be malabsorbed. The malabsorption and resulting steatorrhea are generally not successfully handled by the oral administration of pancreatic lipase. In an effort to control the steatorrhea, the patient may consume less fat than desirable for good health.

Malabsorption of fats leads to nutritional deficiencies and wasting, prompting therapeutic measures to boost fat uptake. In conditions such as CF where the secretion of pancreatic enzymes is insufficient to supply adequate lipases to break down lipids in the gastrointestinal tract, therapeutic measures include the administration of pancreatic enzymes containing lipases. These treatments are insufficient to provide adequate fat digestion to supply the nutritional needs of all such subjects.

Limited body fat is also found frequently in aged and physically stressed individuals. Such individuals also would benefit from methods which increase intestinal fat uptake from dietary sources.

SUMMARY OF THE INVENTION

It has now been discovered that the absorption of dietary fats in the intestine can be increased by increasing the amount of lysophosphatidylcholine in the intestine. It is believed that increased lysophosphatidylcholine acts as a carrier for fats by forming a complex with the fats to increase transport across the membrane into enterocytes which line the intestinal wall. It is believed that increased lysophosphatidylcholine drives the absorption of fats by providing additional material to complex the fat molecules.

According to one aspect of the invention, methods for increasing fat absorption from the intestine of a subject are provided. The methods include administering to a subject in need of such treatment an agent which increases lysophosphatidylcholine in the intestine in an amount effective to increase fat absorption. In certain embodiments the agent comprises an isolated complex of lysophosphatidylcholine and lipid molecules selected from the group consisting of monoglycerides, fatty acids, diglycerides, triglycerides, cholesterols, cholesterol esters, polyglycerol fatty acid esters, sucrose fatty acid esters, sorbitan fatty acid esters and glycerol. In some embodiments the isolated complex includes lysophosphatidylcholine, monoglyceride and fatty acid. Preferably the molar ratio of lysophosphatidylcholine:the sum of monoglyceride and fatty acid in the isolated complex is between 1:3 and 1:12, and more preferably still the molar ratio of lysophosphatidylcholine:the sum of monoglyceride and fatty acid in the isolated complex is between 1:5 and 1:6, more preferably between 1:4:2 and 1:2:4. Still more preferably the isolated complex has a lysophosphatidylcholine:monoglyceride:fatty acid molar ratio selected from the group consisting of 1:4:2, 1:3:3 and 1:3:2. In other embodiments the agent comprises phospholipase $A_2$. Preferably, the agent further comprises a lipid selected from the group consisting of phosphatidylcholine, lysophosphatidylcholine, monoglycerides, fatty acids, diglycerides, triglycerides, cholesterols, cholesterol esters, polyglycerol fatty acid esters, sucrose fatty acid esters, sorbitan fatty acid esters and glycerol. In other preferred embodiments, the agent includes an isolated complex of phospholipase $A_2$ and phosphatidylcholine. Preferably the agent further includes an isolated complex of lysophosphatidylcholine, monoglyceride and fatty acid, particularly wherein the isolated complex has a lysophosphatidylcholine:monoglyceride:fatty acid molar ratio between 1:4:2 and 1:2:4. In still other embodiments, the agent is administered orally. In further embodiments, the serum concentration of lipids is increased. Preferably, the serum concentration of at least one lipid not administered to the subject as part of the agent is increased. In additional embodiments, the agent is formulated to enter the intestine of the subject without substantial degradation; preferably the agent is enteric coated.

According to another aspect of the invention, compositions including phospholipase $A_2$ formulated for oral delivery to a subject are provided. In some embodiments the composition includes phospholipase $A_2$ and a pharmaceutically acceptable carrier. In other embodiments, the composition is enteric coated. In still other embodiments, the compositions also include lipid molecules selected from the group consisting of phosphatidylcholine, lysophosphatidylcholine, monoglycerides, fatty acids, diglycerides, triglycerides, cholesterols, cholesterol esters, polyglycerol fatty acid esters, sucrose fatty acid esters, sorbitan fatty acid esters and glycerol. In yet other embodiments, the compositions include an isolated complex of lysophosphatidylcholine, monoglyceride and fatty acid. Preferably the isolated complex has a lysophosphatidylcholine:monoglyceride:fatty acid molar ratio between 1:4:2 and 1:2:4, more preferably the lysophosphatidylcholine:monoglyceride:fatty acid molar ratio is selected from the group consisting of 1:4:2, 1:3:3 and 1:3:2.

The use of the foregoing compositions in the preparation of medicaments, particularly medicaments for the treatment of cystic fibrosis also is provided.

These and other objects of the invention will be described in further detail in connection with the detailed description of the invention.

DETAILED DESCRIPTION OF THE INVENTION

The invention provides improved methods for increasing fat absorption from the intestine. It has been discovered that increasing the amount of lysophosphatidylcholine in a subject's intestine improves the absorption of dietary fats. Any agent which increases intestinal lysophosphatidylcholine can be used, preferably those which are administered orally to the subject. For example, the agent can be a composition containing lysophosphatidylcholine or a lysophosphatidylcholine precursor. The agent also can be a molecule which catalyzes the production of lysophosphatidylcholine by metabolism or synthesis from precursors of lysophosphatidylcholine. For example, phospholipases catalyze the cleavage of a fatty acid moiety from a phospholipid molecule to generate lysophospholipids, such as lysophosphatidylcholine.

The various lipids useful in the methods of the invention can include fatty acid moieties (or may be fatty acids themselves). Such fatty acids can be unsaturated (monounsaturated or polyunsaturated), or saturated. Where two or more fatty acid moieties exist on a lipid molecule, the fatty acids can be the same or different in chain length, position of one or more double bonds, and degree of unsaturation.

Examples of unsaturated fatty acids which can be used in the composition of this invention are:

| Name | Formula | Carbon atoms:double bonds |
|---|---|---|
| palmitoleic | $C_{16}H_{30}O_2$ | 16:1 |
| oleic | $C_{18}H_{34}O_2$ | 18:1 |
| linoleic | $C_{18}H_{32}O_2$ | 18:2 |
| linoienic | $C_{18}H_{30}O_2$ | 18:3 |
| arachidonic | $C_{20}H_{32}O_2$ | 20:4 |
| eicosapentanoic | $C_{20}H_{30}O_2$ | 20:5 |
| docosahexanoic | $C_{22}H_{32}O_2$ | 22:6 |

| Name | Formula | Carbon atoms:double bonds |
|---|---|---|
| octanoic | $C_8H_{16}O_2$ | 8:0 |
| decanoic | $C_{10}H_{20}O_2$ | 10:0 |
| lauric | $C_{12}H_{24}O_2$ | 12:0 |
| myristic | $C_{14}H_{28}O_2$ | 14:0 |
| palmitic | $C_{16}H_{32}O_2$ | 16:0 |
| stearic | $C_{14}H_{36}O_2$ | 18:0 |

The monounsaturated, polyunsaturated and saturated fatty acids can be present individually or in combination. That is, the fatty acid constituents of one or more of the lipid molecules can be identified or they can be a mixture of the mono-, polyunsaturated and/or saturated members of the preferred fatty acid families.

Lipids useful according to the invention in lipid complexes with lysophosphatidyl-cholines include phosphatidylcholines, fatty acids, monoglycerides, and cholesterol and fatty acid esters thereof. Cholesterol is known to form stable complexes with lysophosphatidyl-choline, including liposome structures (see, e.g. Ramsammy and Brockerhoff, *J. Biol. Chem.* 257:3570–3574, 1982).

The agent, which increases intestinal lysophosphatidylcholine, can include other lipid molecules such as polyglycerol fatty acid esters, sorbitan fatty acid esters, sucrose fatty acid esters and glycerol. Such compounds are described in U.S. Pat. No. 4,849,132. A polyglycerol fatty acid ester molecule consists of mono-, di- or polyesters of fatty acids with 4–12 polymerized glycerol molecules. A sorbitan fatty acid ester molecule consists on mono-, di- or polyesters of fatty acids with sorbitol, sorbitan and sorbide. A sucrose fatty acid ester molecule consists of mono-, di- or polyesters of fatty acids with sucrose. As with the acyl group of monoglyceride, the fatty acids/acyl groups of polyglycerol fatty acid ester, sorbitan fatty acid ester and sucrose fatty acid ester preferably have carbon chains of 8–22 carbon atoms and 1–4 unsaturations. As above, the specific acyl groups, purity, and mixture of agent molecules useful in the invention depend on the requirements of the individual user.

The agent can also include non-lipid molecules which may affect the physical form and/or physiological properties of the agent. These include, for example, bile salts and bicarbonate, which aid in the formation of colloidal particles of a lipid complex.

Exemplary lipid complexes including lysophosphatidylcholine useful in the invention are described in U.S. Pat. Nos. 4,874,795, 5,314,921, 5,571,517, 5,707,873 and 5,741,822. It is preferred that an isolated complex of lysophosphatidylcholine and lipid molecules contain lysophosphatidylcholine, monoglyceride and fatty acid. Preferably a complex of lysophosphatidylcholine, monoglyceride and fatty acids is constituted in the molar ratio of lysophosphatidylcholine:the sum of monoglyceride and fatty acid of about 1:3 to 1:12. Most preferably, the molar ratio of lysophosphatidylcholine:the sum of monoglyceride and fatty acid is about 1:5–1:6. It is also preferred that the individual components of the complex are present in particular molar ratios in relation to one another. Thus, it is preferred that the molar ratios of lysophosphatidylcholine:monoglyceride:fatty acid are 1:4:2–1:2:4. Most preferably, the molar ratios of lysophosphatidylcholine:monoglyceride:fatty acid are either 1:4:2, 1:3:3 or 1:3:2.

Mixtures of lipid complex colloidal particles including lysophosphatidylcholine, or precursors thereof, can be made from individual colloidal particle formulations. Such mixtures have different colloidal particle sizes which can affect their emptying time from the stomach and which have different fat processing and uptake rates from the small intestine to the bloodstream. These colloidal particle mixtures, thus, have prolonged uptake attributes.

The methods of the invention also include administering a composition which contains both a precursor of lysophosphatidylcholine (e.g. phosphatidylcholine) and/or lysophosphatidylcholine itself, and an enzyme for converting lysophosphatidylcholine precursors to lysophosphatidylcholine (e.g. phospholipase $A_2$). The enzyme can convert precursors of lysophosphatidylcholine in the composition itself, as well as precursors of lysophosphatidylcholine which exist in the intestine. The preferred precursor for the preparation of lysophosphatidylcholine is phosphatidylcholine, a phospholipid composed of a polar hydrophilic head group of choline, phosphate and glycerol linked to a nonpolar hydrophobic tail group consisting of two fatty acid molecules. Phosphatidylcholine may be obtained with specific fatty acid groups, or with a mixture of various fatty acid groups. For example, Phospholipon® 80 and/or Phospholipon® 90 (American Lecithin, Oxford, Conn.), is a mixture of phosphatidylcholine molecules having a variety of fatty acid acyl groups linked to the polar head group.

Preparation of lysophosphatidylcholine can be accomplished according to any method known in the art, including synthesis of lysophosphatidylcholine from smaller lipid molecules, and hydrolysis of phosphatidylcholine. Preferably, preparation of lysophosphatidylcholine is carried out by an enzymatic process, followed by separation of the lysophosphatidylcholine product from the other components of the reaction mixture. Methods for separation and purification of lipid molecules such as lysophosphatidylcholine from a complex reaction mixture are well known in the art.

Preferably, phosphatidylcholine is hydrolyzed to lysophosphatidylcholine by the action of phospholipase $A_2$, which severs the ester bond linking a fatty acid group to the 2-position of the glycerol in the head group of phosphatidylcholine. Phospholipase $A_2$ may be purified from a variety of sources, or it may be obtained from commercial sources (e.g. Lecitase™ 10 L, Novo Nordisk, Denmark). For full activity, phospholipase $A_2$ is believed to require the presence of $Ca^{2+}$ ions in the reaction mixture. While typically there is a low level of $Ca^{2+}$ ions in the commercial phospholipase $A_2$ preparations such that phospholipase $A_2$ is active, it is preferred that $Ca^{2+}$ ions be added to any composition which contains $PLA_2$ for full activity. It should be noted that $Ca^{2+}$ ions are depleted from the reaction mixture by ionic bonding with the acid group of fatty acids liberated during hydrolysis of phosphatidylcholine. Therefore it is preferred that sufficient $Ca^{2+}$ ions are added to the reaction mixture to maintain full activity of phospholipase $A_2$. It is preferable that the calcium ion concentration be supplemented to achieve a molar ratio of calcium ion:phosphatidylcholine of at least 1:1 when using $PLA_2$ to hydrolyze phosphatidylcholine.

It will be recognized by persons of ordinary skill in the art that other ions may be substituted for the $Ca^{2+}$ ions in order to maintain full activity of the phospholipase $A_2$ enzyme. While not all ions may substitute for $Ca^{2+}$ ions in this reaction, the specific type and concentration of ions adequate for maintenance of phospholipase $A_2$ activity easily may be tested by one of ordinary skill in the art.

Preferred methods for making lysophosphatidylcholine by hydrolysis of phosphatidylcholine using phospholipase $A_2$ are provided in U.S. Pat. No. 5,716,814. According to these methods, complete or nearly complete conversion of phosphatidylcholine to lysophosphatidylcholine can be accomplished by $PLA_2$ in the presence of one or more auxiliary molecule which improve access of an aqueous phosphatidylcholine lipid matrix by phospholipase $A_2$. Preferred auxiliary molecules include monoglyceride, diglyceride, polyglycerol fatty acid ester, sucrose fatty acid ester, sorbitan fatty acid ester and glycerol. Most preferably, the auxiliary molecule is monoglyceride. The acyl groups of such auxiliary molecules preferably have carbon chain links from 8 to 22 carbon atoms and 1 to 4 unsaturations. The specific acyl groups, purity, and mixture of auxiliary molecules useful in the invention depends on the requirements of the individual user. Any combination or type of auxiliary molecules is contemplated by the invention, so long as the hydrolysis of phosphatidylcholine is enhanced. One of ordinary skill in the art will be familiar with additional methods for preparing lysophosphatidylcholine.

The suitability of various combinations of lipids, enzymes and accessory molecules in the methods of the invention can be assessed in human studies or in standard animal models of digestion and nutrient uptake. For example, a test composition which increases lysophosphatidylcholine in the intestine can be administered orally to test subjects along with radioactively or stable isotope labeled lipid tracer molecules. Blood samples can be taken at intervals from the subject and the samples analyzed for intestinal absorption of the radioactively or stable isotope labeled lipids. The rate and amount of intestinal absorption can then be compared to control subjects that did not receive the test composition which increases lysophosphatidylcholine in the intestine. Compositions which increase lipid uptake are useful in the methods disclosed herein. Additional methods for assessing the intestinal lipid transport properties of a test composition are well known in the nutritional and medical arts.

The compositions useful in the methods described herein are administered by a method which does not permit significant introduction of the lysophosphatidylcholine-increasing agent into the bloodstream of a patient. Preferably, administration is oral. For compositions containing phospholipase $A_2$, administration is oral.

When administered, the compositions of the present invention can be administered in pharmaceutically acceptable preparations. Such preparations may routinely contain pharmaceutically acceptable concentrations of salt, buffering agents, preservatives, compatible carriers, and the like, and optionally other therapeutic ingredients. Such therapeutic ingredients include drugs and pancreatic enzymes. Preferably compositions which contain enzymes are enteric coated for oral delivery.

The various components of the preparations preferably are pharmaceutically acceptable, but non-pharmaceutically acceptable components, including food grade components when used for oral delivery are not excluded from the scope of the invention. Such salts include, but are not limited to, those prepared from the following acids: hydrochloric, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1–2% W/V); citric acid and a salt (1–3% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

Preferred carriers are pharmaceutically-acceptable carriers, although food grade carriers may be used for oral delivery. The term pharmaceutically-acceptable carrier means one or more compatible solid or liquid fillers, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the lipid molecules and complexes useful in the present invention, and with each other, in a manner such that there is no interaction which would substantially impair the desired pharmaceutical efficacy. Formulations of lipids and lipid-containing complexes suitable for administration to mammals (including especially oral administration) can be found in Remington's Pharmaceutical Sciences, Mack Publishing Co., Easton, Pa.

The compositions may conveniently be presented in unit dosage form and may be prepared by any of the methods well known in the art of pharmacy. All methods include the step of bringing the compositions useful in the methods of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of lysophosphatidylcholine or lysophosphatidylcholine-increasing compositions described herein. Other compositions include suspensions in aqueous liquors or non-aqueous liquids such as a syrup, an elixir, or an emulsion.

As used herein, an effective amount of lysophosphatidylcholine, a complex containing lysophosphatidylcholine, or a lysophosphatidylcholine-increasing composition is a dosage large enough to produce the desired therapeutic effect of increasing intestinal fat uptake. An effective amount is not, however, a dosage so large as to cause adverse side effects. Generally, an effective amount may vary with the subject's age, condition, weight and sex, as well as the extent of the condition being treated, and can be determined by one of skill in the art. The dosage may be adjusted by the individual practitioner in the event of any complication.

All references disclosed herein are incorporated by reference in their entirety.

Those skilled in the art will recognize, or be able to ascertain using no more than routine experimentation, many equivalents to the specific embodiments of the invention described herein. Such inventions are intended to be encompassed by the following claims.

I claim:

1. An enteric coated composition for oral delivery comprising phospholipase $A_2$ and lipid molecules selected from the group consisting of phosphatidylcholine, lysophosphatidylcholine, monoglycerides, fatty acids, diglycerides, triglycerides, cholesterols, cholesterol esters, polyglycerol fatty acid esters, sucrose fatty acid esters, sorbitan fatty acid esters and glycerol.

2. The composition of claim 1, further comprising a pharmaceutically acceptable carrier.

3. The composition of claim 1, wherein the lipid molecules are an isolated complex of lysophosphatidylcholine, monoglyceride and fatty acid.

4. The composition of claim 3 wherein the isolated complex has a lysophosphatidylcholine:monoglyceride:fatty acid molar ratio between 1:4:2 and 1:2:4.

5. The composition of claim 4 wherein the isolated complex has a lysophosphatidylcholine:monoglyceride:fatty acid molar ratio selected from the group consisting of 1:4:2, 1:3:3 and 1:3:2.

* * * * *